US012678618B2

(12) United States Patent
Melius et al.

(10) Patent No.: US 12,678,618 B2
(45) Date of Patent: Jul. 14, 2026

(54) ANCHORING HOLDING TOOL

(71) Applicant: BIOTRONIK SE & Co. KG, Berlin (DE)

(72) Inventors: Matthew Melius, Milwauki, OR (US); Andrew B. Kibler, Lake Oswego, OR (US); Julia Khoury Valentine, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 337 days.

(21) Appl. No.: 18/289,250

(22) PCT Filed: Apr. 27, 2022

(86) PCT No.: PCT/EP2022/061167
§ 371 (c)(1),
(2) Date: Nov. 2, 2023

(87) PCT Pub. No.: WO2022/233669
PCT Pub. Date: Nov. 10, 2022

(65) Prior Publication Data
US 2025/0352786 A1 Nov. 20, 2025

Related U.S. Application Data

(60) Provisional application No. 63/184,490, filed on May 5, 2021.

(30) Foreign Application Priority Data

May 31, 2021 (EP) ..................................... 21176770

(51) Int. Cl.
*A61N 1/05* (2006.01)
*A61N 1/372* (2006.01)

(52) U.S. Cl.
CPC ........... *A61N 1/0558* (2013.01); *A61N 1/372* (2013.01)

(58) Field of Classification Search
CPC .......... A61N 1/0558; A61N 2001/0578; A61N 1/057; A61N 2001/058; A61N 1/05;
(Continued)

(56) References Cited

U.S. PATENT DOCUMENTS 4,462,401 A * 7/1984 Burgio ................. A61N 1/0541
607/137
6,895,283 B2 5/2005 Erickson et al.
(Continued)

OTHER PUBLICATIONS

International Search Report and Written Opinion dated Jul. 22, 2022, for International Application No. PCT/EP2022/061167, 15 pages.

*Primary Examiner* — Mohamed G Gabr
(74) *Attorney, Agent, or Firm* — FBT Gibbons LLP

(57) ABSTRACT

An anchor holding tool is used for holding, during an implantation procedure, a lead anchor device. The lead anchor device is used for anchoring a lead in a patient. The anchor holding tool includes a holding tip for engaging with the lead anchor device, and a handle connected to the holding tip. The holding tip generally extends along a longitudinal axis for receiving the lead anchor device along the longitudinal axis on the holding tip. The handle extends at an angle with respect to the longitudinal axis from the holding tip. The holding tip forms an inner face shaped to abut with an anchor body of the lead anchor device. The inner face includes a concave shape extending about the longitudinal axis for receiving the anchor body of the lead anchor device.

17 Claims, 8 Drawing Sheets

(58) Field of Classification Search
CPC   A61N 1/36017; A61B 17/282; A61B 5/0215;
A61B 17/29
See application file for complete search history.

(56)                     References Cited

U.S. PATENT DOCUMENTS

| | | | | |
|---|---|---|---|---|
| 9,561,363 | B2 | 2/2017 | Skubitz et al. | |
| 2005/0004590 | A1* | 1/2005 | Waters ................. | A61B 17/282 |
| | | | | 606/170 |
| 2008/0243220 | A1 | 10/2008 | Barker | |
| 2011/0264181 | A1 | 10/2011 | Hamilton | |

* cited by examiner

ANCHORING HOLDING TOOL

The instant text concerns an anchoring holding tool for holding, during an implantation procedure, a lead anchor device for anchoring a lead in a patient. The instant text further concerns an implantation system comprising an anchoring holding tool and a lead anchor device. In addition, the instant text concerns the use of an anchor holding tool of an implantation system for holding a lead anchor device for anchoring a lead in a patient.

Generally, in neuro-stimulation applications, such as in spinal cord stimulation, an implantable medical device in the shape of an electrode device having a lead may be used for providing for a nerve or neuro stimulation, e.g. in the vicinity of the spinal cord.

Spinal cord stimulation may provide for a pain therapy by injecting electrical pulses to a targeted position of the spine. For this, an electrode device must be implanted into a patient by for example introducing the electrode device into the epidural space of the spinal column such that the electrode device with an electrode arrangement arranged thereon is located at the targeted position for injecting electrical pulses into tissue at the targeted position.

During implantation the electrode device is introduced e.g. into the spinal (vertebral) column at a point of entry, which is accessed through a surgical access incision. The lead herein needs to be axially fixed to tissue in the vicinity of the point of entry into the spinal column, such that after implantation the electrode device remains in place and is axially secured with respect to the spinal column.

For axial fixation of the lead of an electrode device at an implantation site, generally a lead anchor device is used, which for example is slit upon the lead and is sutured to fascia in the region of the spinal column at the point of entry into the spinal column. The lead anchor device for example may form an inner channel through which the lead extends, a fastening element serving to axially fix the lead with respect to the lead anchor device, such that upon suturing the lead anchor device to the fascia the lead is fastened and secured within the patient.

When implanting a medical device in the shape of an electrode device having a lead into a patient, there is a general desire to keep surgery as easy and minimally invasive as possible. In particular, an incision through which the lead is implanted and introduced into the patient beneficially should be small to reduce impact on the patient and to minimize surgical recovery time following the implantation operation.

At the same time, a lead anchor device must, for allowing a suturing to surrounding tissue, be accessed at the implantation site and must be held in place at the implantation site, wherein the incision may be deep, and slippery fluids at the implantation site may cause manual manipulation and stabilization of the lead anchor device to be challenging during operation. In particular, a secure holding of the lead anchor device allowing for a manipulation and stabilization of the lead anchor device at the implantation site may not be easily achieved using common surgical tools, such as surgical clips or the like.

A medical device in the shape of an electrode device having a lead for implantation into a patient may be a so-called paddle electrode. Different designs of paddle electrodes are known, for example, from U.S. Pat. Nos. 6,895, 283 and 9,561,363.

It is an object of the instant invention to provide an anchor holding tool, an implantation system and a use of an anchor holding tool of an implantation system that allow for an easy and comfortable manipulation and stabilization of a lead anchor device for anchoring a lead in a patient.

This object is achieved by means of an anchor holding tool comprising the features of claim 1.

Accordingly, an anchor holding tool for holding, during an implantation procedure, a lead anchor device for anchoring a lead in a patient comprises a holding tip for engaging with the lead anchor device, and a handle connected to the holding tip. The holding tip generally extends along a longitudinal axis for receiving the lead anchor device along the longitudinal axis on the holding tip, the handle extending at an angle with respect to the longitudinal axis from the holding tip.

The holding tip forms an inner face which is shaped to abut with an anchor body of the lead anchor device. According to an embodiment, the anchor body of the lead anchor device may have a generally cylindrical shape, the inner face of the holding tip having a shape which is complementary to the shape of the anchor body, such that the anchor body may be received on the holding tip at the inner face for holding and stabilizing the lead anchor device at an implantation site.

In particular, the inner face may have a concave shape extending about the longitudinal axis for receiving the anchor body of the lead anchor device. For example, the holding tip at its inner face facing the anchor body of the lead anchor device hence is rounded in a concave manner, such that the holding tip may be brought into engagement with the anchor body of the lead anchor device for holding the lead anchor device in place at an implantation site.

According to an embodiment, the holding tip may have a generally semi-circumferential shape for receiving the anchor body of the lead anchor device there within.

The anchor holding tool serves to hold a lead anchor device at an implantation site such that the lead anchor device may be manipulated and stabilized for anchoring a lead in a patient. In particular, by means of the holding tool an operator may access and hold the lead anchor device such that the lead anchor device may be sutured to tissue at the implantation site, in particular the fascia in the vicinity of the spinal column, and a lead guided on the lead anchor device may be axially fixed to the lead anchor device.

The anchor holding tool may be easy and cost-efficient to manufacture. The anchor holding tool furthermore may be sterilizable, disposable and light-weight, such that a low-cost tool for a reliable use during an implantation procedure for implanting a lead into a patient is provided.

The anchor holding tool comprises a holding tip for acting onto the lead anchor device. The holding tip may be brought into engagement with the lead anchor device, such that by means of the holding tip the lead anchor device may be hold in place and stabilized, such that in particular a suture may be established to fixate the lead anchor device to tissue, and a lead may be secured to the lead anchor device for providing for an axial fixation of the lead at the implantation site.

The handle of the anchor holding tool allows an operator to hold the anchor holding tool manually, wherein the handle is angled with respect to the holding tip. This allows to access the lead anchor device by means of an external tool, for example for applying a suture to fixate the lead anchor device, or for fixing a fastening element on the lead anchor device for axially securing the lead to the lead anchor device for example using a torque wrench.

The holding tip generally extends along a longitudinal axis such that the lead anchor device, which has a generally longitudinal shape, may be received on the holding tip along the longitudinal axis. The handle extends at an angle, measured with respect to the longitudinal axis, from the holding tip, wherein the angle may lie in a range in between 5° and 60°, for example between 5° and 45°, beneficially between 5° and 30°. By having the handle extend at an oblique angle from the holding tip it is ensured that the handle is not in the way when accessing the implantation site by means of an external tool, for example for applying a suture or for fixing a fastening element to secure a lead to the lead anchor device.

In one embodiment, the holding tip comprises an access opening for accessing the lead anchor device using an external tool. The lead anchor device may comprise a fastening element for example in the shape of a screw, which can be fastened in order to provide for an axial fixation of a lead to the lead anchor device. The manipulation of the fastening element herein, during operation, takes place for example by a torque wrench, such that the fastening element needs to be accessed during operation from the outside. The anchor holding tool herein may be shaped such that it may be brought into engagement with the lead anchor device at the location of the fastening element of the lead anchor device, the access opening in the holding tip allowing to access the fastening element on the lead anchor device and to manipulate the fastening element by an external tool, for example a torque wrench.

The access opening herein is dimensioned such that the external tool can be brought into operative connection with the fastening element through the access opening of the holding tip, and can be manipulated by operating the external tool, for example by rotating the external tool, for example in the shape of a torque wrench.

In one embodiment, the inner face comprises at least one first form-fit element for forming a form-fit connection with said anchor body of the lead anchor device. The form-fit element may for example have the shape of a groove which may be brought into engagement with a corresponding, second form-fit element formed on the anchor body of the lead anchor device, the second form-fit element in this case for example having the shape of a ridge protruding from the anchor body. Vice versa, the first form-fit element may be formed as a ridge which is to engage with a second form-fit element formed on the anchor body in the shape of a corresponding groove.

By receiving the lead anchor device on the holding tip, hence, a form-fit connection in between the anchor holding tool and the lead anchor device may be established. The lead anchor device hence may be grabbed using the anchor holding tool in that the holding tip is engaged with the anchor body of the lead anchor device to form a form-fit connection in between the holding tip and the lead anchor device, such that the lead anchor device may be placed at the implantation site and may be manipulated at the implantation site.

In one embodiment, the at least one first form-fit element extends parallel to said longitudinal axis. A corresponding second form-fit element formed on the anchor body of the lead anchor device in this case also extends longitudinally along the longitudinal axis such that a form-fit connection may be formed in between the first form-fit element of the holding tip and the second form-fit element of the anchor body of the lead anchor device.

In another embodiment, the at least one first form-fit element extends circumferentially about the longitudinal axis. A corresponding second form-fit element formed on the anchor body of the lead anchor device in this case also extends circumferentially such that a form-fit connection in between the form-fit elements may be formed for connecting the holding tip to the lead anchor device.

Multiple first form-fit elements may be provided on the holding tip, the first form-fit elements for example each extending along the longitudinal axis or circumferentially about the longitudinal axis, wherein it also is possible that some first form elements extend longitudinally along the longitudinal axis and other form-fit elements extend circumferentially about the longitudinal axis. Corresponding, complementary second form-fit elements in each case are formed on the anchor body of the lead anchor device.

In another aspect, an implantation system comprises an anchor holding tool of the kind described above and a lead anchor device for anchoring a lead in a patient. The lead anchor device comprises an engagement portion for engaging with the holding tip of the anchor holding tool. By engaging the holding tip with the engagement portion of the lead anchor device, hence, a connection in between the anchor holding tool and the lead anchor device may be established, such that the lead anchor device may be held in place at an implantation site during implantation of a medical device having a lead, in particular an electrode device for implantation for example in the region of a spinal column of a patient.

In one embodiment, the engagement portion comprises at least one second form-fit element for forming a form-fit connection with the holding tip. The at least one second form-fit element is formed complementary to a corresponding first form-fit element formed on the inner face of the holding tip. The at least one second form-fit element for example may have the shape of a ridge or a groove, which extends longitudinally along the longitudinal axis or circumferentially about the longitudinal axis.

In one embodiment, the lead anchor device comprises an anchor body made of a silicone material. The anchor body has a generally longitudinal shape, wherein the anchor body may be received on the holding tip of the anchor holding tool to extend along the longitudinal axis.

In one embodiment, the lead anchor device forms an inner channel extending along the longitudinal axis for receiving a lead of an implantable medical device. During an implantation operation, the lead is implanted into a patient, for example in the region of the spinal column of the patient. For axially fixing the lead at the implantation site, the lead anchor device is slit onto the lead and placed at the implantation site, wherein the anchor holding tool is used to stabilize the anchor holding tool at the implantation site to allow for a manipulation on the lead anchor device at the implantation site. For sliding the lead anchor device onto the lead, herein, the lead is inserted into the inner channel of the lead anchor device, such that the lead extends through the inner channel and the lead anchor device may be axially moved on the lead to locate the lead anchor device in the region of a point of entry at a region of interest, e.g., the spinal column.

In one embodiment, the lead anchor device comprises a fastening element, for example in the shape of a screw, for fastening the lead with respect to the lead anchor device. The fastening element may be brought into operative connection with the lead, such that the lead is axially fixed with respect to the lead anchor device. Hence, by fixating the lead anchor device at the implantation site, for example by suturing the lead anchor device to fascia at the implantation site, the lead is axially fixed within the patient, such that for example an electrode arrangement arranged on the lead is held immovably at a targeted position for injecting electrical pulses, for example for spinal cord stimulation applications.

The holding tip of the anchor holding device, in one embodiment, comprises an access opening formed as a through hole on the holding tip, such that the anchor holding tool may be placed on the lead anchor device at the location of the fastening element and the fastening element of the lead anchor device may be accessed through the access opening of the holding tip by means of an external tool, in particular a torque wrench.

In yet another aspect the anchor holding tool of the implantation system is used for holding the lead anchor device for anchoring a lead in a patient.

The various features and advantages of the present invention may be more readily understood with reference to the following detailed description and the embodiments shown in the drawings. Herein, FIG. 1 shows a view of an electrode device connected to a stimulation device in an implanted state in the area of the spine of a patient;

Subsequently, embodiments of the invention shall be described in detail with reference to the drawings. In the drawings, like reference numerals designate like structural elements.

It is to be noted that the embodiments are not limiting for the invention, but merely represent illustrative examples.

Figure 1:
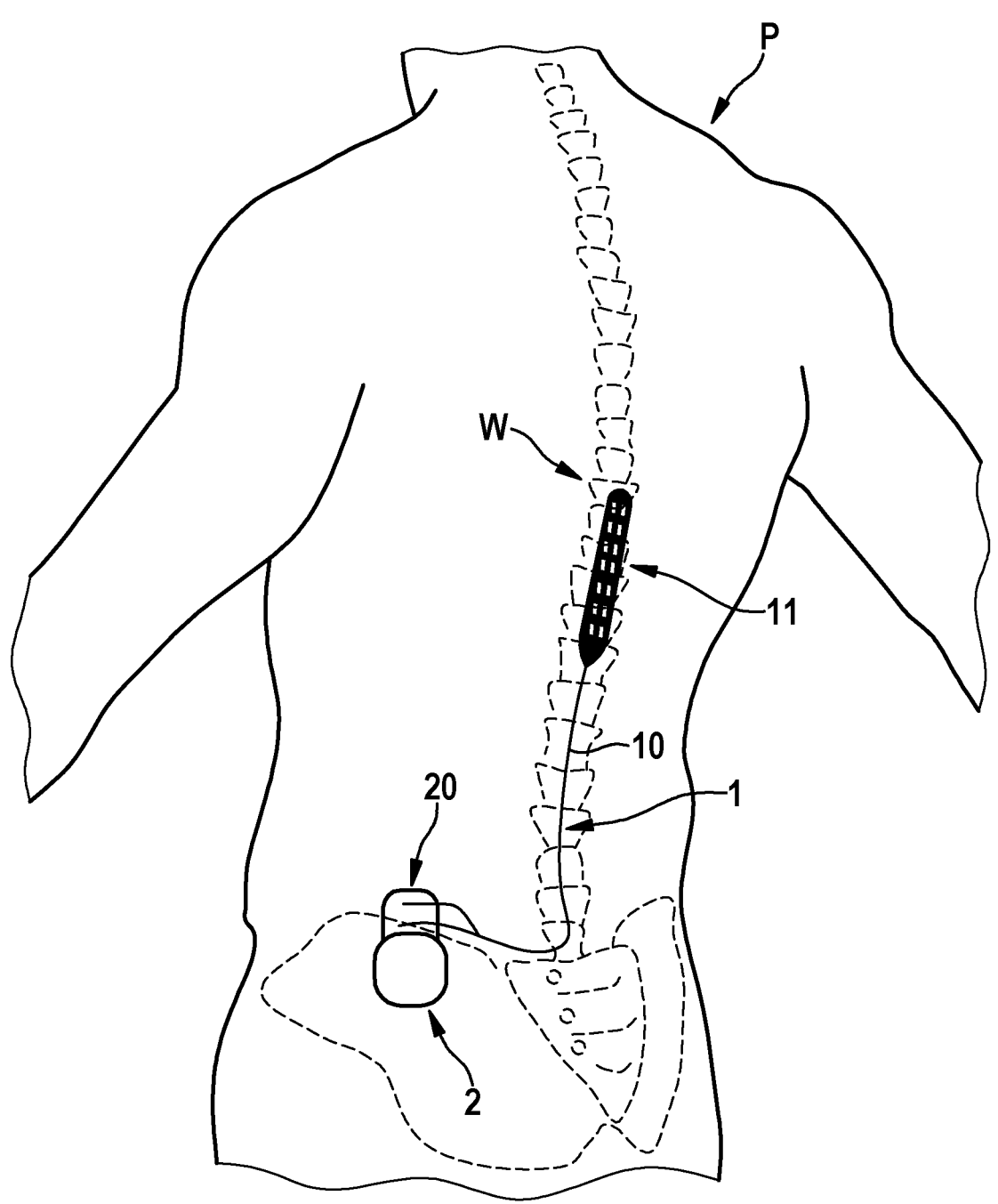
Figure 2:
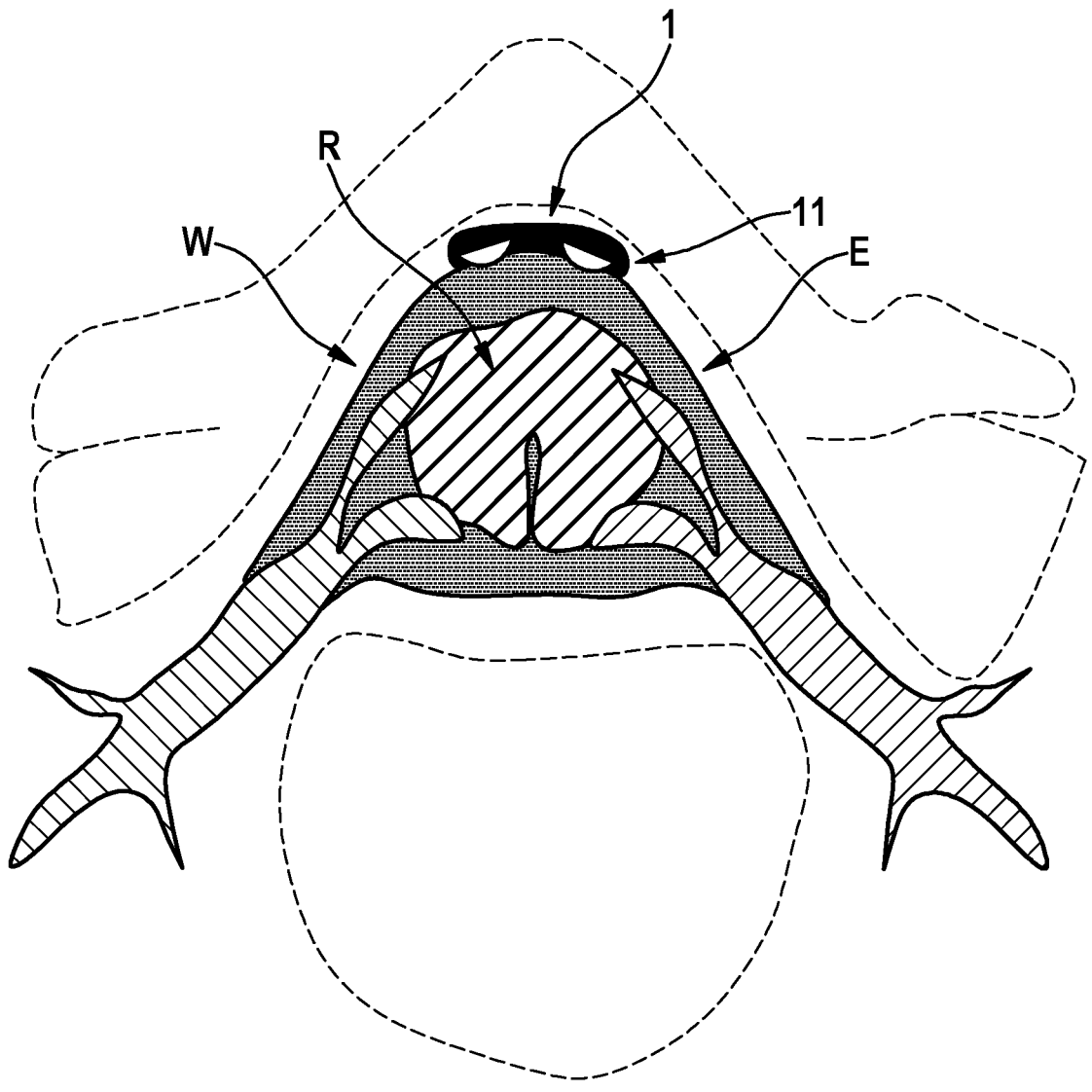
FIG. 2 shows a view of the electrode device in the epidural space in the region of the spinal column.

An implantable medical device in the shape of an electrode device 1, as shown in an embodiment in FIGS. 1 and 2, may for example be formed as a so-called paddle electrode and comprises a lead 10 and an electrode end 11 connected to the lead 10, a plurality of electrode elements being attached to the electrode end 11 for emitting stimulation energy e.g. in the region of the spinal column W of a patient P.

In an implanted state the electrode device 1 at a proximal end of the lead 10 is connected to a connector block 20 of a stimulation device 2, via which stimulation energy can be delivered to the electrode device 1 and radiated via the electrode arrangement arranged on the electrode end 11 to stimulate the spinal cord R in the region of the spinal column W.

As can be seen from the sectional view of FIG. 2, in the embodiment shown the electrode device 1 is implanted with the electrode end 11 in the epidural space E in the region of the spinal column W of the patient P in such a way that the electrode end 11 is located in the region of the spinal cord R and can thus introduce stimulation energy in a directed manner into the spinal cord R in order to effect nerve stimulation in the region of the spinal cord R.

Figure 3:
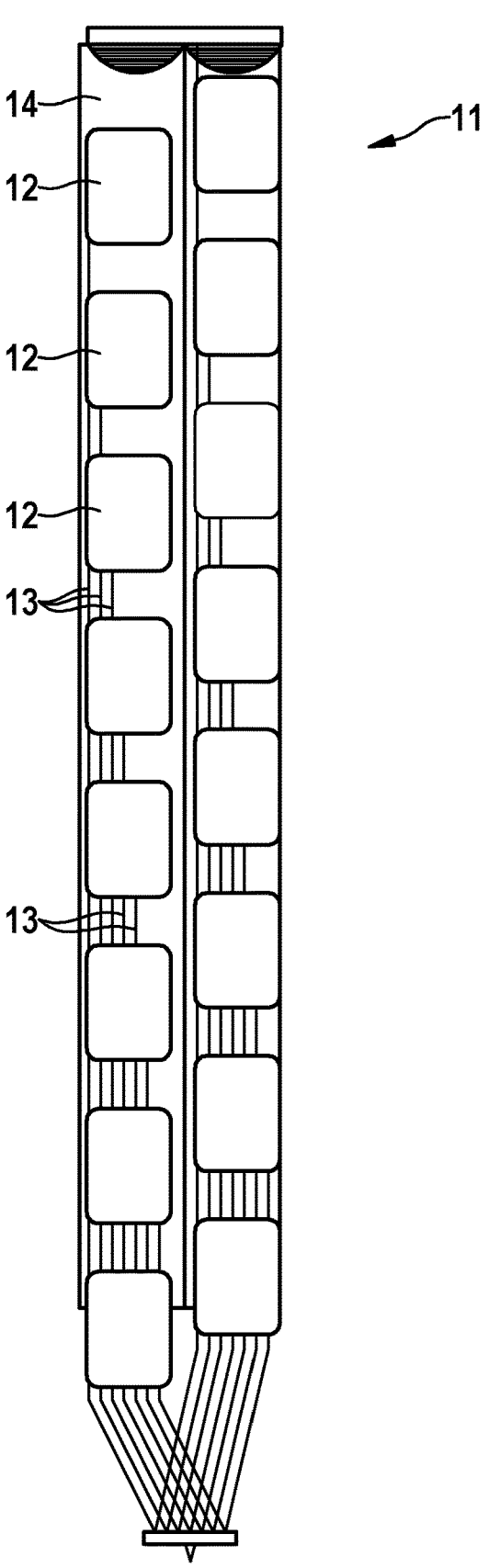
FIG. 3 shows a view of a flattened end of an embodiment of an electrode device.

While the lead 10 for example comprises a circular (isodiametric) cross-section, the electrode device 1 is flattened in the area of the electrode end 11 which, as can be seen in FIG. 3, carries a plurality of electrode elements 12, which may be evenly or unevenly spaced on the electrode end 11 in such a way that stimulation energy can be fed in a directed manner for example into the spinal cord R of a patient P.

As further illustrated in FIG. 3, each electrode element 12 is connected to a supply line 13, wherein each electrode element 12 can be connected to the stimulation device 2 via an associated, individual supply line 13 and thus may be supplied with stimulation energy via the stimulation device 2 to emit an electrical signal. The supply lines 13 are jointly routed as a cable strand in the lead 10 in an encapsulated manner to the stimulation device 2.

The electrode elements 12 are arranged on a carrier element 14, but are exposed with a surface facing outwards and can therefore come into contact with surrounding tissue when the electrode device 1 is implanted in a patient.

An implantable medical device in the shape of an electrode device 1 as shown in FIGS. 1 to 3 may for example be used for pain therapy by means of spinal cord stimulation. For this, the electrode device 1 is implanted into the patient such that the lead 10 is introduced into the epidural space E of the spinal column W, as shown in FIGS. 1 and 2, such that the electrode end 11 is placed at a targeted position of the spinal column W for injecting electrical pulses into the spinal cord R.

Figure 4A:
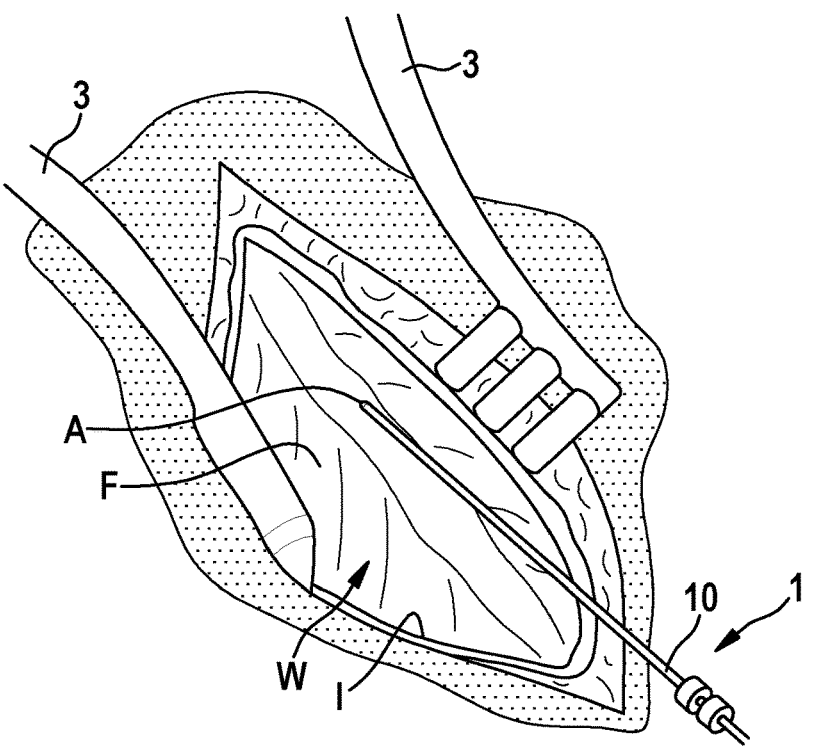
FIG. 4A shows a view of an implantation operation for implanting a lead in the region of the spinal column of a patient.
Figure 4B:
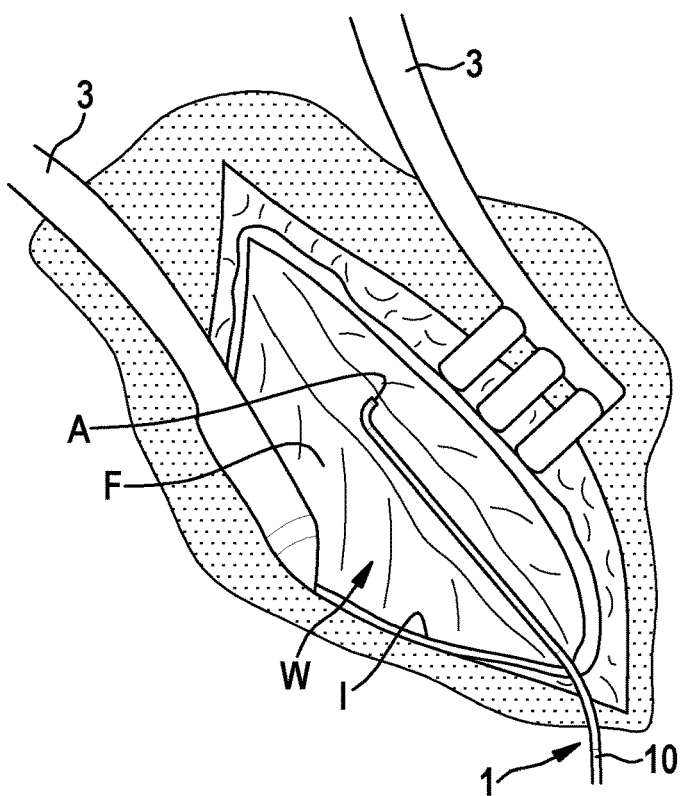
FIG. 4B shows the lead introduced into the spinal column at a point of entry during the implantation procedure.

Referring now to FIGS. 4A to 4D, during implantation an incision I is formed at a surgical implantation site to access the spinal column W, wherein the lead 10 of the electrode device 1 is introduced at a point of entry A into the spinal column W and hence is inserted into the epidural space E of the spinal column W. By advancing the lead 10 into the spinal column W the electrode arrangement of the electrode device 1 is placed at the targeted position, as this is shown in FIGS. 4A and 4B.

During surgery, the incision I is held open by means of surgical tools 3, such that an access to the spinal cord W at the point of entry A is provided.

Figure 4C:
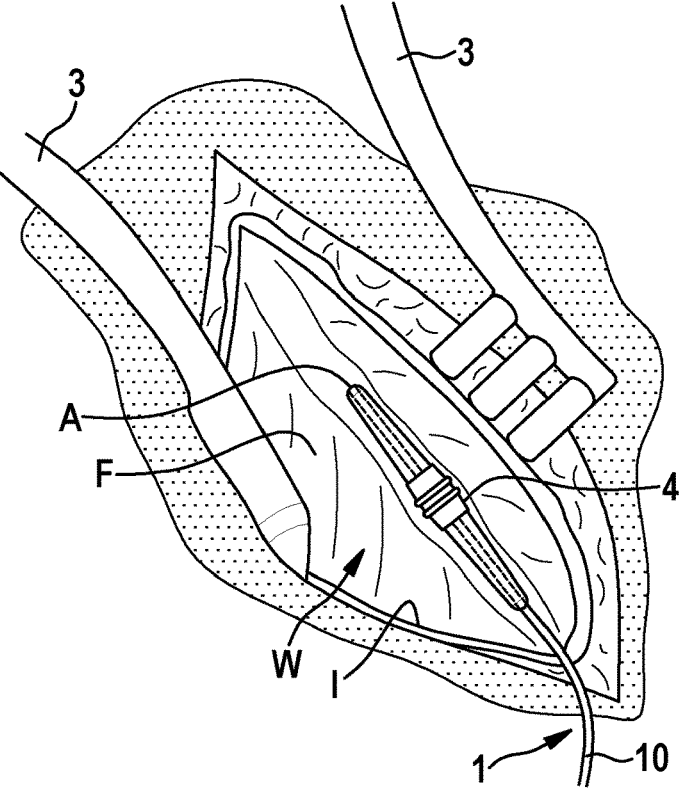
FIG. 4C shows a lead anchor device placed on the lead for axially fixing the lead in the vicinity of the point of entry.
Figure 4D:
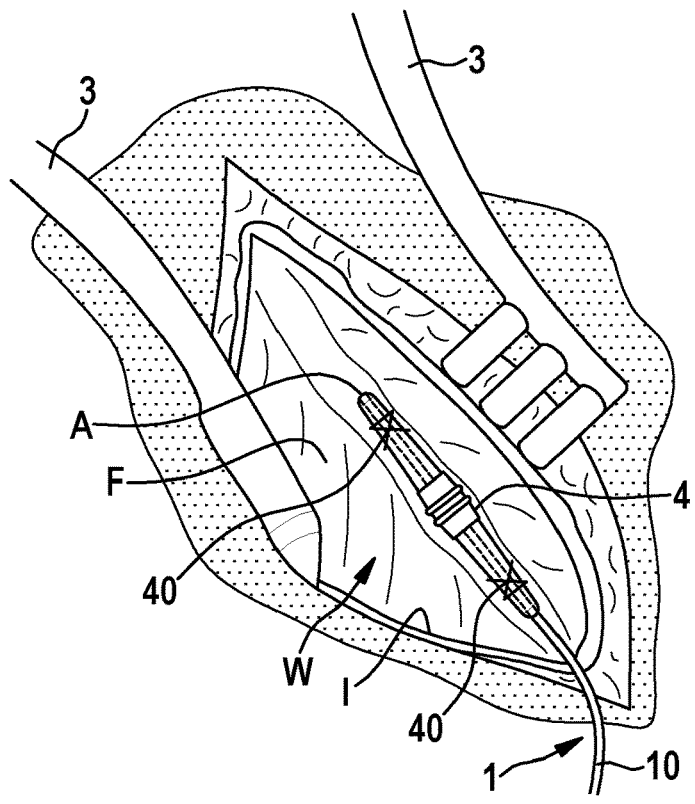
FIG. 4D shows the lead anchor device sutured to fascia in the region of the point of entry.

Once the lead 10 has been advanced into the spinal column W such that the targeted position is reached, a lead anchor device 4 is slit onto the lead 10 towards the point of entry A, as this is shown in FIG. 4C. The lead anchor device 4 serves to anchor the lead 10 on the fascia F in the region of the spinal column W, the lead anchor device 4 providing for an axial fixation of the lead 10 with respect to the spinal column W such that the electrode device 1 with its electrode arrangement is held in position for exerting a stimulation action at the targeted position of the spinal column W.

For providing for an axial fixation, the lead anchor device 4 is sutured, by means of sutures 40, to the fascia F such that the lead anchor device 4 is fixed to tissue at the spinal column W. By axially fixing the lead 10 to the lead anchor device 4, hence, the lead 10 is securely fastened and held in place, such that the surgical incision I can now be closed and implantation be completed.

Figure 5:
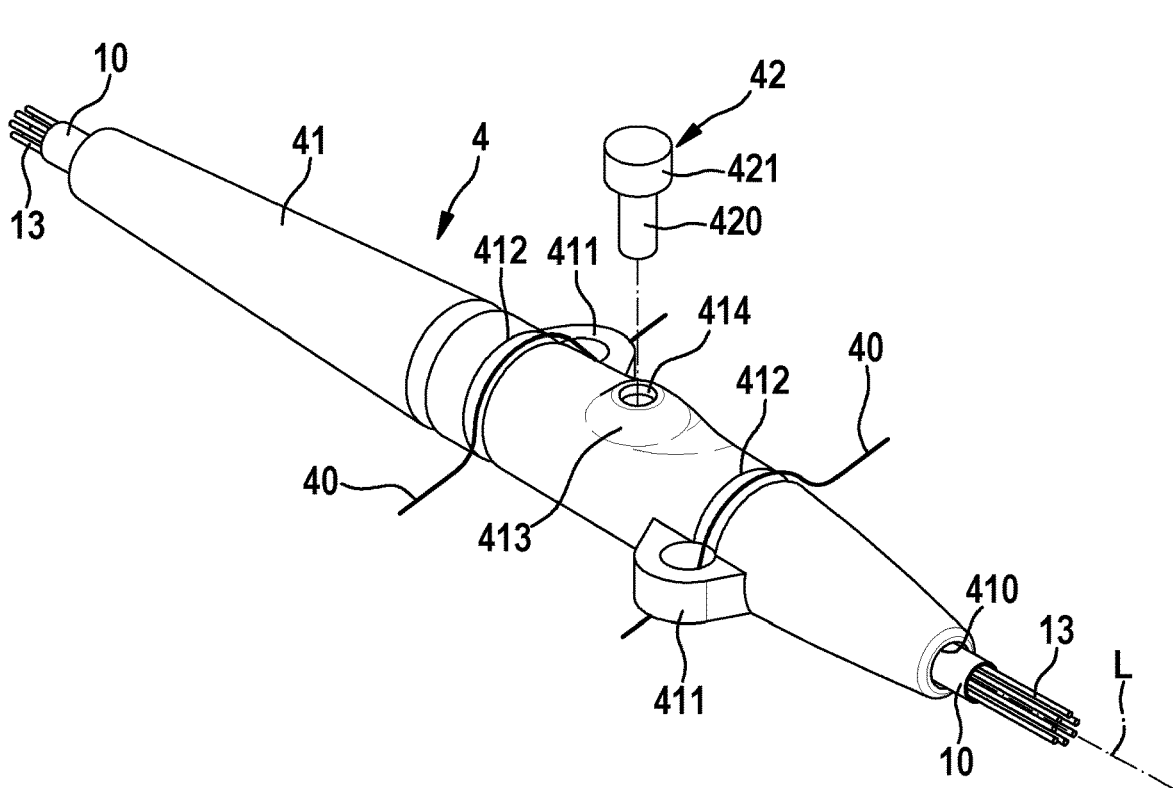
FIG. 5 shows a view of an embodiment of a lead anchor device.

FIG. 5 shows an embodiment of a lead anchor device 4, the lead anchor device 4 comprising an anchor body 41 made of for example a silicone material. The lead anchor device 4, with its anchor body 41, has a generally longitudinal shape and extends along a longitudinal axis L, an inner channel 410 being formed within the anchor body 41 for receiving a lead 10 there within.

Eyelets 411 are formed on the anchor body 41, and grooves 412 extend circumferentially about the anchor body 41 in the region of the eyelets 411. Sutures 40 may be passed through the eyelets 411 and may be placed in the grooves 412, such that the lead anchor device 4 may be secured to tissue at an implantation site using sutures 40.

A fastening element 42 in the shape of a screw is placed within an opening 414 formed on the anchor body 41. The fastening element 42 comprises a threaded shaft 420 engaging with the opening 414 and a head 421 which may be accessed by means of an external tool, in particular a torque wrench, such that the fastening element 42 may be screwed into the anchor body 41 for axially fixing a lead 10 received in the inner channel 410 with respect to the anchor body 41 and hence with respect to the anchor device 4.

As this is apparent from FIGS. 4A to 4D, during implantation of an electrode device 1 the lead anchor device 4 needs to be slit onto the lead 10 inserted into the patient and needs to be fastened to tissue at an implantation site. This takes place within an incision I, which may be deep, wherein in addition slippery fluids at the implantation site may make manual manipulation and stabilization of the lead anchor device 4 a challenging task.

Figure 6:
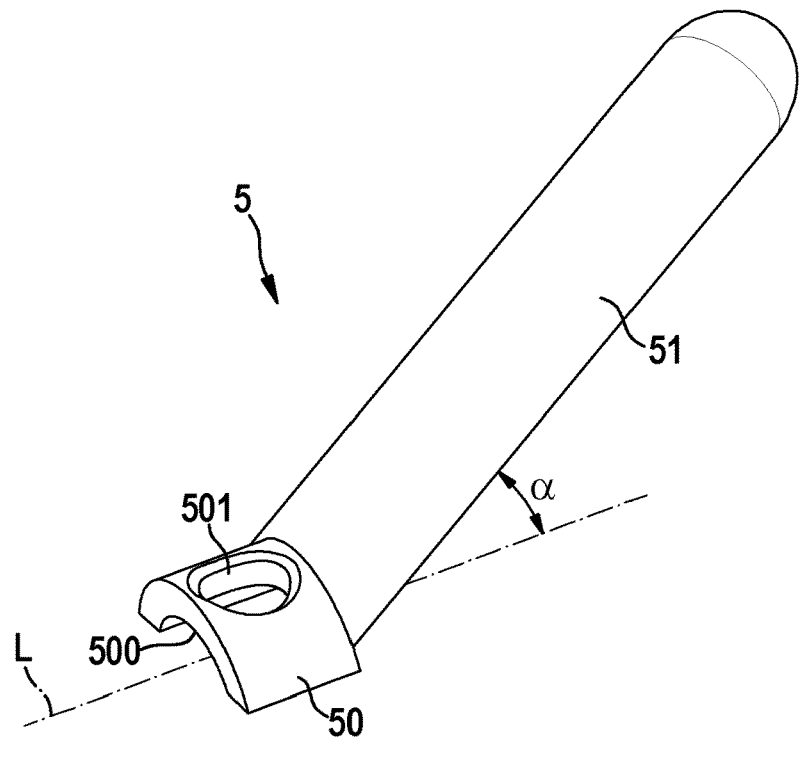
FIG. 6 shows a view of an embodiment of an anchor holding tool.

To facilitate implantation and placement of the lead anchor device 4, an anchor holding tool 5 is provided, as it is shown in one embodiment in FIG. 6.

The anchor holding tool 5 comprises a holding tip 50, which serves to operatively connect to the anchor body 41 of the lead anchor device 4, and a handle 51 which extends at an angle with respect to the holding tip 50.

The holding tip 50 extends generally along the longitudinal axis L, the holding tip 50 forming an inner face 500 which semi-circumferentially extends about the longitudinal axis L, the holding tip 50 hence having a concave shape for receiving and engaging with the anchor body 41 of the lead anchor device 4.

An access opening 501 is formed on the holding tip 50, the access opening 501 extending through the holding tip 50 and allowing to access the fastening element 42 by means of an external tool when the anchor holding tool 5 is in engagement with the lead anchor device 4. The anchor holding tool 5 herein is shaped and configured to abut with the lead anchor device 4 at an engagement portion 413 in the region of the fastening element 42, as this is visible from FIG. 5, such that the fastening element 42 with its head 421 is placed within the access opening 501 of the holding tip 50 when the anchor holding tool 5 is placed on the lead anchor device 4. Via the access opening 501 an external tool, for example a torque wrench, hence may be brought into operative connection with the head 421 of the fastening element 42, such that the fastening element 42 may be manipulated, in particular by screwing the fastening element 42 into the anchor body 41 for axially fixing the lead 10 to the anchor body 41.

The handle 51 extends at an angle α with respect to the longitudinal axis L, as this is shown in FIG. 6. The angle α may lie in the range between 5° and 60°, beneficially between 5° and 45°, for example at 30°. Because the handle 51 is obliquely angled with respect to the holding tip 50 and in particular does not extend at a perpendicular angle with respect to the holding tip 50 (i.e., with respect to the longitudinal axis L), the handle 51—which may be grabbed by a user to hold the lead anchor device 4 in place by means of the anchor holding tool 5—does not hinder access of the access opening 501 and hence the fastening element 42 by means of an external tool, and further does not hinder a suturing of the lead anchor device 4 to tissue at the implantation site.

By means of the holding tip 50 a form-fit connection in between the anchor holding tool 5 and the lead anchor device 4 may be established, such that the lead anchor device 4 may be securely held and stabilized using the anchor holding tool 5.

Figure 7A:
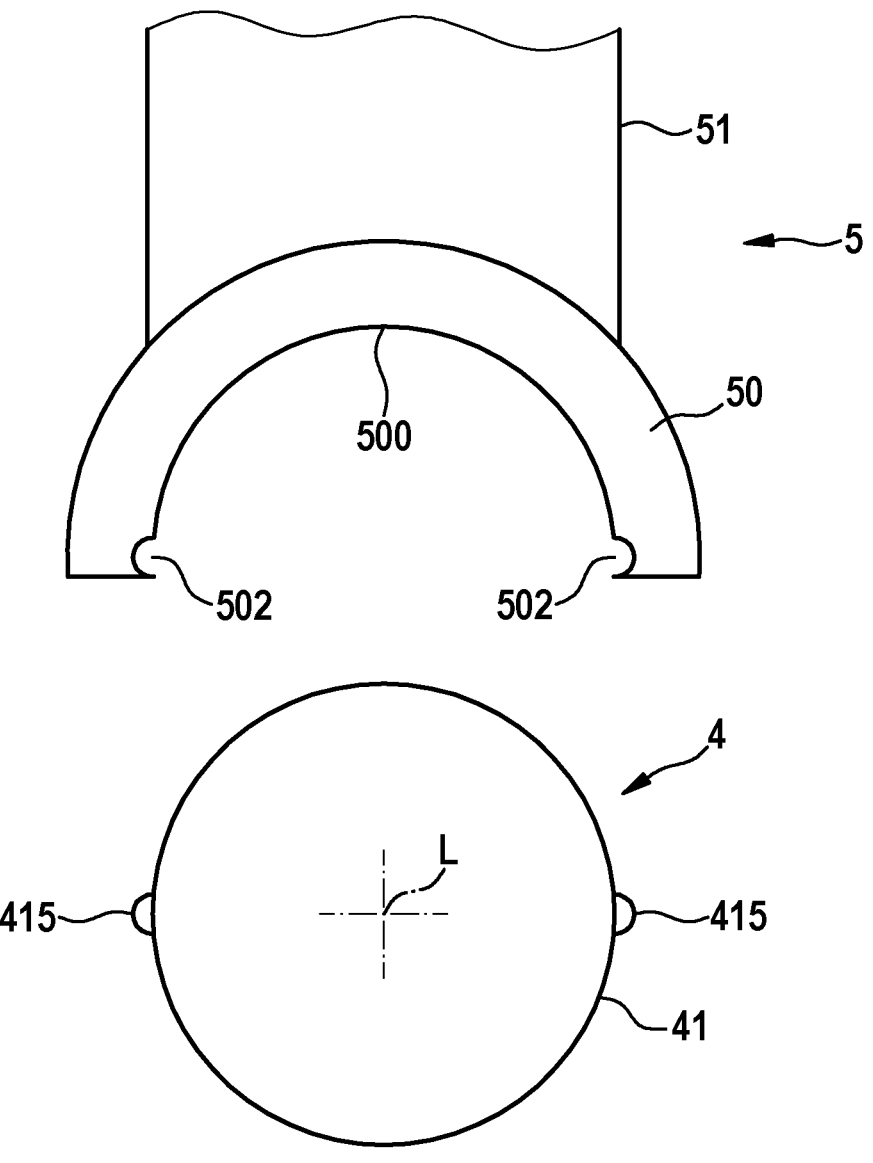
FIG. 7A shows a schematic front view of an embodiment of an anchor holding tool together with a lead anchor device.
Figure 7B:
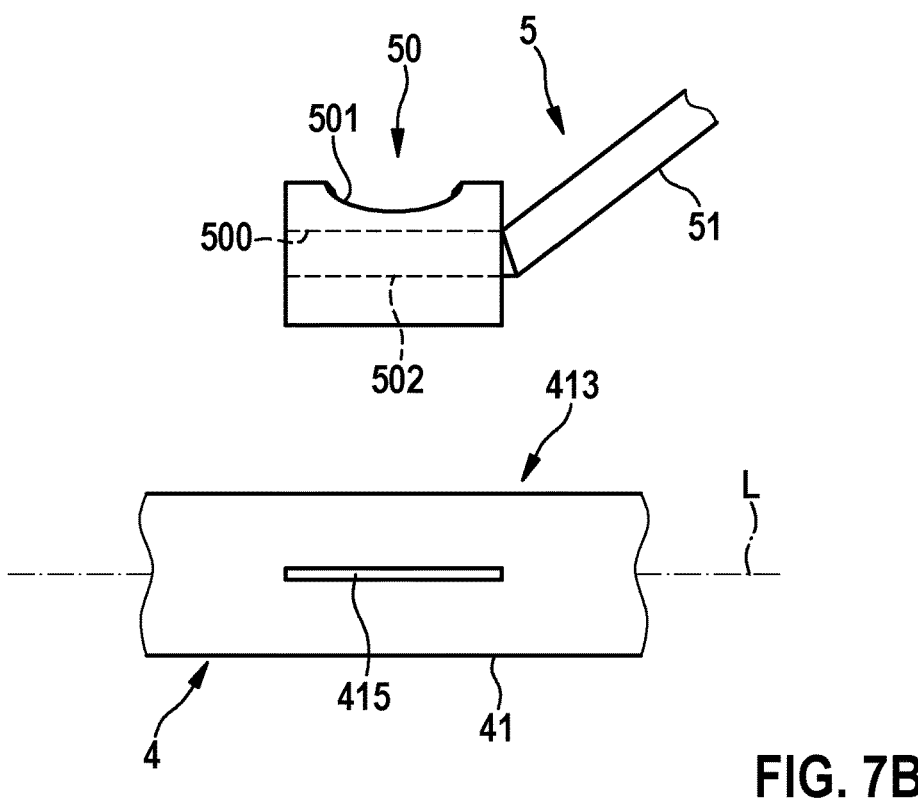
FIG. 7B shows a schematic side view of the embodiment of FIG. 7A.

For this, as it is shown in one embodiment in FIGS. 7A and 7B, first form-fit elements 502 in the shape of grooves may be formed on the inner face 500 of the holding tip 50, the first form-fit elements 502 in the shape of grooves serving to engage with corresponding, complementary second form-fit elements 415 in the shape of ridges formed on the anchor body 41 of the lead anchor device 4.

In the embodiment of FIGS. 7A and 7B, herein, the form-fit elements 415, 502 extend longitudinally in parallel to the longitudinal axis L.

Figure 8:
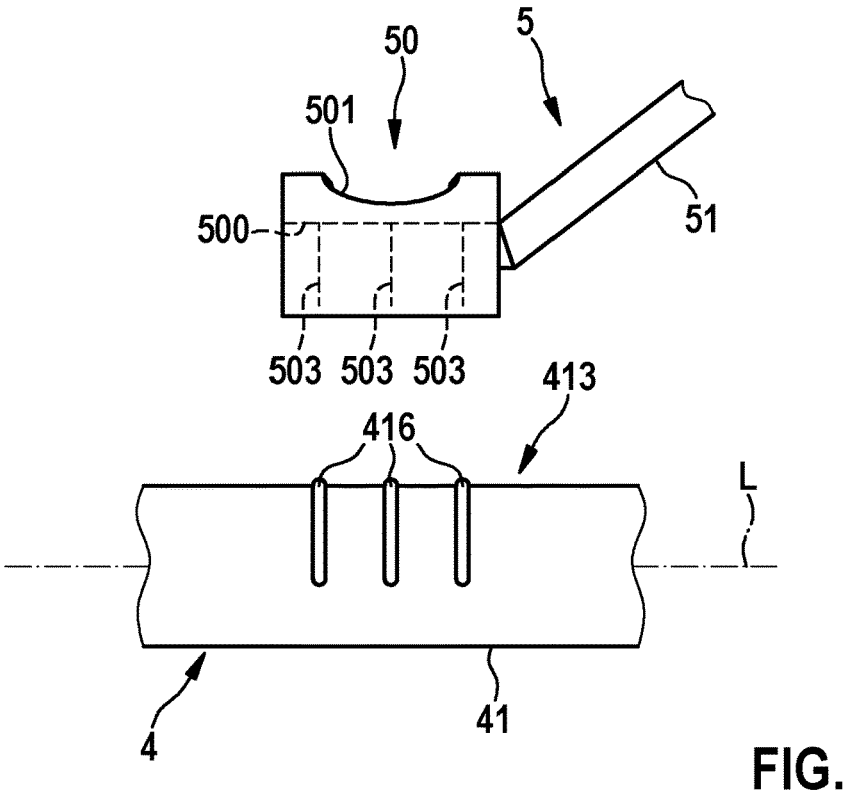
FIG. 8 shows a schematic side view of another embodiment of an anchor holding tool together with a lead anchor device.

In contrast, in the embodiment of FIG. 8 first form-fit elements 503 in the shape of grooves are formed on the inner face 500 of the holding tip 50, the form-fit elements 503 extending circumferentially about the longitudinal axis L. Corresponding second form-fit elements 416 in the shape of ridges are formed on the anchor body 41 of the lead anchor device 4, the second form-fit elements 416 extending circumferentially about the longitudinal axis L on the anchor body 41.

First Form-fit elements 502, 503 on the holding tip 50 may be combined such that both longitudinally extending first form-fit elements 502 as well as circumferentially extending first form-fit elements 503 are formed on the holding tip 50. Likewise, second form-fit elements 415, 416 on the side of the anchor body 41 may be combined, such that both longitudinally extending second form-fit elements 415 and circumferentially extending second form-fit elements 416 are formed on the anchor body 41.

A lead anchor device as described herein may generally be used to secure any lead within a patient, also for applications other than spinal cord stimulation.

An electrode device having a lead may have the shape of a paddle electrode, but may be also designed as an isodiametric electrode carrying ring electrodes on an electrode end.

LIST OF REFERENCE NUMERALS

1 Implantable medical device (electrode device)
10 Lead
11 Electrode end
12 Electrode element
13 Supply line
14 Carrier element
2 Stimulation device
20 Connector block
3 Surgical tool
4 Lead anchor device
40 Suture
41 Anchor body
410 Inner channel
411 Eyelet
412 Groove
413 Engagement portion
414 Opening
415, 416 Second Form-fit element
42 Fastening element (screw)
420 Shaft
421 Head

9

5 Anchor holding tool
50 Holding tip
500 Inner face
501 Access opening
502, 503 First Form-fit element
51 Handle
α Angle
A Point of entry
E Epidural space
F Fascia
I Incision
L Longitudinal axis
P Patient
R Spinal cord
W Spinal column

The invention claimed is:

1. A kit comprising:
(a) a lead (10), the lead (10) including an electrode (11);
(b) a lead anchor device (4), the lead anchor device (4) including an anchor body (41), the anchor body (41) being configured to be positioned about the lead (10), the lead anchor device (4) being further securable to tissue of a patient (P);
(c) an anchor holding tool (5) for holding, during an implantation procedure, the lead anchor device (4) for anchoring the lead (10) in a patient (P), the anchor holding tool (5) comprising:
(i) a holding tip (50), wherein the holding tip (50) forms an inner face (500) shaped to abut with the anchor body (41), wherein the inner face (500) comprises a concave shape extending about the longitudinal axis (L) for receiving said anchor body (41) such that the holding tip (50) is structured to complement a structure of the anchor body (41) to thereby engage the lead anchor device (4), and
(ii) a handle (51) connected to the holding tip (50), wherein the holding tip (50) generally extends along a longitudinal axis (L) for receiving the lead anchor device (4) along the longitudinal axis (L) on the holding tip (50), the handle (51) extending at an angle (α) with respect to the longitudinal axis (L) from the holding tip (50).

2. The kit according to claim 1, wherein said angle (α) lies in a range between 5° and 60°.

3. The kit according to claim 1, wherein the holding tip (50) comprises an access opening (501) for accessing the lead anchor device (4) using an external tool.

4. The kit according to claim 1, wherein at least one first form-fit element (502, 503) is formed on the inner face (500) for forming a form-fit connection with said anchor body (41) of the lead anchor device (4).

5. The kit according to claim 4, wherein said at least one first form-fit element (502, 503) is formed as a groove or a ridge.

6. The kit according to claim 4, wherein said at least one first form-fit element (502, 503) extends parallel to said longitudinal axis (L) or circumferentially about said longitudinal axis (L).

7. The kit according to claim 4, wherein some first form elements (502, 503) extend longitudinally along the longitudinal axis and other form-fit elements (502, 503) extend circumferentially about the longitudinal axis.

8. A kit according to claim 1, wherein the lead anchor device (4) comprises an engagement portion (413) for engaging with the holding tip (50) of the anchor holding tool (5).

9. The kit according to claim 8, wherein the engagement portion (413) comprises at least one second form-fit element (415, 416) for forming a form-fit connection with the holding tip (50).

10. The kit according to claim 9, wherein said at least one second form-fit element (415, 416) is formed as a ridge or a groove.

11. The kit according to claim 8, wherein the lead anchor device (4) comprises an anchor body (41) made of a silicone material.

12. The kit according to claim 8, wherein the lead anchor device (4) forms an inner channel (410) extending along the longitudinal axis (L) for receiving a lead (10) of an implantable medical device (1).

13. The kit according to claim 8, wherein the lead anchor device (4) comprises a fastening element (42) for fastening a lead (10) of an implantable medical device (1) with respect to the lead anchor device (4).

14. The kit according to claim 13, wherein the fastening element (42) is a screw.

15. A method of using the kit of claim 8, comprising:
(a) engaging the engagement portion (413) with the holding tip (50) of the anchor holding tool (5); and
(b) anchoring the lead (10) in the patient (P) with the lead anchor device (4).

16. A kit comprising:
(a) a lead (10), the lead (10) including an electrode (11);
(b) a lead anchor device (4), the lead anchor device (4) including an anchor body (41), the anchor body (41) being configured to be positioned about the lead (10), the lead anchor device (4) being further securable to tissue of a patient (P); and
(c) an anchor holding tool (5) for holding, during an implantation procedure, the lead anchor device (4) for anchoring the lead (10) in a patient (P), the anchor holding tool (5) comprising:
(i) a holding tip (50), wherein the holding tip (50) forms an inner face (500) shaped to abut with the anchor body (41), wherein the inner face (500) comprises a concave shape extending about the longitudinal axis (L) for receiving a complementary shape of said anchor body (41), wherein the holding tip (50) is configured to engage the anchor body (41) while the lead (10) is positioned within the anchor body (41), and
(ii) a handle (51) connected to the holding tip (50), wherein the holding tip (50) generally extends along a longitudinal axis (L) for receiving the lead anchor device (4) along the longitudinal axis (L) on the holding tip (50), the handle (51) extending at an angle (α) with respect to the longitudinal axis (L) from the holding tip (50).

17. An anchor holding tool (5) for holding, during an implantation procedure, a lead anchor device (4) for anchoring a lead (10) in a patient (P), the anchor holding tool (5) comprising:
(a) a holding tip (50) for engaging with the lead anchor device (4), wherein the holding tip (50) comprises an access opening (501) for accessing the lead anchor device (4) using an external tool; and
(b) a handle (51) connected to the holding tip (50), wherein the holding tip (50) generally extends along a longitudinal axis (L) for receiving the lead anchor device (4) along the longitudinal axis (L) on the holding tip (50), the handle (51) extending at an angle (α) with respect to the longitudinal axis (L) from the holding tip (50), wherein the holding tip (50) defines a thickness, wherein the inner face (500) comprises a concave shape extending about the longitudinal axis (L) for receiving said anchor body (41) of the lead anchor device (4), wherein the access opening (501) is formed through the thickness of the holding tip.

\* \* \* \* \*